(12) United States Patent
Fan et al.

(10) Patent No.: US 10,107,719 B2
(45) Date of Patent: Oct. 23, 2018

(54) MASS-BALANCING ARRANGEMENT AND MICROTOME USING SAME

(71) Applicant: Leica Microsystems Ltd. Shanghai, Shanghai (CN)

(72) Inventors: Zheguang Fan, Shanghai (CN); Xiao Zhou, Shanghai (CN)

(73) Assignee: Leica Microsystems Ltd. Shanghai, Shanghai (CN)

( * ) Notice: Subject to any disclaimer, the term of this patent is extended or adjusted under 35 U.S.C. 154(b) by 479 days.

(21) Appl. No.: 14/287,003

(22) Filed: May 24, 2014

(65) Prior Publication Data

US 2015/0047490 A1    Feb. 19, 2015

(30) Foreign Application Priority Data

Aug. 19, 2013  (CN) .......................... 2013 1 0364613

(51) Int. Cl.
| | |
|---|---|
| *G01N 1/06* | (2006.01) |
| *F16F 15/22* | (2006.01) |
| *F16F 15/26* | (2006.01) |

(52) U.S. Cl.
CPC .......... *G01N 1/06* (2013.01); *G01N 2001/065* (2013.01); *Y10T 83/6499* (2015.04); *Y10T 83/8824* (2015.04)

(58) Field of Classification Search
CPC ............... Y10T 403/54; Y10T 83/6499; Y10T 83/8824; F04B 47/026; F16F 15/22; F16F 15/26; F16F 15/261; G01N 2001/065; G01N 1/06

USPC ........ 173/89, 118, 202–203, 49; 74/592, 25, 74/522.5, 54; 267/173–174; 83/707, 83/731, 628; 248/593–592
See application file for complete search history.

(56) References Cited

U.S. PATENT DOCUMENTS 3,272,022 A * 9/1966 Spinner .................... B23Q 5/34
                                                                74/53
4,126,069 A    11/1978 Shimonaka
4,702,464 A    10/1987 Bauer et al.
(Continued)

FOREIGN PATENT DOCUMENTS

DE    3347238 C1    2/1985
EP    0048604 A1 *  8/1981
(Continued)

*Primary Examiner* — Sean Michalski
*Assistant Examiner* — Fernando Ayala
(74) *Attorney, Agent, or Firm* — Hodgson Russ LLP (57) ABSTRACT

A mass-balancing arrangement comprises an adjustably preloaded spring member (14); a pivotably mounted lever (16; 31) for compensating different inertial forces in combination with the spring member (14); a first drawing member (24) connecting a movable mass to the lever (16); a second drawing member (17) connecting the spring member (14) to the lever (16); and a first roller (15) for deflecting the first drawing member (24). The lever (16; 31) has an upper lever arm (19; 32) and a lower lever arm (20; 33), one being sector-shaped and the other cam-shaped. The upper lever arm is connected to the movable mass through the first drawing member (24), and the lower lever arm is connected to the spring (14) through the second drawing member (24). Two torques produced at the upper and lower lever arms are kept balanced. The balanced mass may be an object carriage of a microtome.

12 Claims, 6 Drawing Sheets

(56) References Cited

U.S. PATENT DOCUMENTS

| | | | | | |
|---|---|---|---|---|---|
| 5,456,128 | A | * | 10/1995 | Thunker | B41F 21/05 101/409 |
| 5,881,626 | A | * | 3/1999 | Kiene | G01N 1/06 83/615 |
| 5,996,919 | A | * | 12/1999 | Murayama | A01K 89/015 242/261 |
| 7,677,523 | B2 | * | 3/2010 | Stokkermans | B23Q 11/0025 248/123.11 |
| 2003/0167892 | A1 | | 9/2003 | Foerderer | |
| 2013/0186248 | A1 | | 7/2013 | Heid | |

FOREIGN PATENT DOCUMENTS

| | | | |
|---|---|---|---|
| EP | 0048604 | | 3/1982 |
| EP | 0603127 | | 12/1993 |
| GB | 0254943 | * | 7/1926 |
| GB | 254943 | | 7/1926 |
| GB | 2304928 | * | 8/1995 |

* cited by examiner

MASS-BALANCING ARRANGEMENT AND MICROTOME USING SAME

CROSS REFERENCE TO RELATED APPLICATIONS

This application claims priority of Chinese patent application number 201310364613.9 filed Aug. 19, 2013, the entire disclosure of which is incorporated by reference herein.

FIELD OF THE INVENTION

This invention generally relates to microtomes, in particular, a mass-balancing arrangement for the microtome.

BACKGROUND OF THE INVENTION

Microtomes are used to cut thin sections from samples. These sections are subsequently placed on a coverslip, suitably processed, and then examined under a microscope. A microtome, in particular, a rotary microtome generally includes an object carriage. The object carriage carries a specimen holder that holds a specimen to be cut. The object carriage is moved up and down, by a drive means, in a vertical path on the rotary microtome. During this vertical movement, the specimen is passed over a cutter fixedly arranged on the rotary microtome.

In conventional rotary microtomes, control of the vertical cutting movement generally takes place by means of a transmission mechanism which is driven by a hand wheel. The transmission mechanism transforms turning movement of the hand wheel into vertical movement of the object carriage. In this type of drive, the moveable masses of the rotary microtome, which includes the specimen and all of the moveable components of the microtome, are alternately and repeatedly accelerated and decelerated. Gravitation accelerates the moveable masses during a first half-turn of the hand wheel (downward movement of the object carriage) and decelerates the moveable masses during the second half-turn of the hand wheel (upward movement of the object carriage). Thus, only a force reduced by the force of gravitation is required on the hand wheel during the downward movement of the object carriage, and a force increased by the force of gravitation is required during the upward movement.

To balance these undesired accelerations and decelerations, rotary microtomes include a mass-balancing arrangement. The mass-balancing arrangement generally comprises an asymmetrical balancing weight which is integrated into the hand wheel. However, where the moveable masses of the rotary microtome are relatively large, the balancing weight must be dimensioned to be correspondingly large, thereby increasing the bulk of the microtome. Furthermore, an asymmetrically formed balancing weight may produce undesirable vibrations in the rotary microtome during relatively fast upward and downward movements of the object carriage. Vibrations in the microtome inevitably cause the specimens to be cut in such a way that they are unusable.

U.S. Pat. No. 5,881,626 discloses a mass-balancer for balancing the movable masses of the microtome. The mass-balancer has a pre-tensioned, adjustable spring element and a pivotably mounted lever for compensating different inertial forces of the microtome in combination with the spring element. A drawing element connects the lever to the object carriage. The mass-balancer is indirectly connected to the drive mechanism by the drawing element. In particular, the lever has, extending from a pivot pin, an upper lever arm and a lower lever arm, which are arranged at an angle with respect to each other. The force acting on the object carriage can be adapted appropriately in all positions by the leverages provided by the lever arms and the tension spring acting on the lower lever arm.

However, in U.S. Pat. No. 5,881,626, when the object carriage moves downwardly, the spring is further tensioned, the effective length (moment arm) of the lower lever arm is shortened gradually, while the spring force, which changes with the moving distance and angles, is increased in accordance with a trigonometric function. Thus, it is impossible that the product of the moment arm and the spring force remains constant. On the other hand, the weight or acting force of the object carriage mass remains constant, but the moment arm of the object carriage mass is changed, so the product of the moment arm and the acting force of the object carriage mass cannot be constant. Under this circumstance, it is impossible to reach a perfect balance between the two sides of the lever.

SUMMARY OF THE INVENTION

Accordingly, it is therefore a general objective of the invention to provide a microtome which will obviate or minimize difficulties of the type previously described.

It is a specific object of the invention to provide a microtome having a mass-balancing arrangement that enable the movable masses to reach a perfect balance.

To realize the objects, the present invention provides a mass-balancing arrangement comprising: a pre-loaded, adjustable spring member; a pivotably mounted lever for compensating different inertial forces in combination with the spring member; a first drawing member for connecting a movable mass to the lever; a second drawing member for connecting the spring member to the lever; and a first roller for deflecting the first drawing member, wherein the lever has an upper lever arm and a lower lever arm, one of the upper lever arm and the lower lever arm is sector-shaped, and the other one of the upper lever arm and the lower lever arm is cam-shaped, the upper lever arm is connected to the movable mass through the first drawing member, and the lower lever arm is connected to the spring through the second drawing member, wherein the spring member is adjustably fixed at a first end thereof, and is connected to the lower lever arm at a second end thereof through the second drawing member, and wherein two torques, produced at both sides of the lever, are kept balanced with each other.

Preferably, it further comprises a second roller for deflecting the second drawing member.

Preferably, the upper lever arm is sector-shaped and has a first outer end surface of a circular-arc shape, while the lower lever arm is cam-shaped and has a second outer end surface of a cam-surface shape.

Preferably, the first drawing member is fixedly coupled to a distal end of the first outer end surface of the upper lever arm, while the second drawing member is fixedly coupled to a distal end of the second outer end surface of the lower lever arm.

Preferably, the upper lever arm is cam-shaped and has a third outer end surface of a cam-surface shape, while the lower lever arm is sector-shaped and has a fourth outer end surface of a circular-arc shape.

Preferably, the first drawing member is fixedly coupled to a distal end of the third outer end surface of the upper lever arm, while the second drawing member is fixedly coupled to a distal end of the fourth outer end surface of the lower lever arm.

Preferably, the movable mass is an object carriage of a microtome.

Preferably, the spring member is connected to a base frame at its first end through an adjustable tensioning screw.

Preferably, the contour of the cam of the lower lever arm or the upper lever arm is designed so that it enables the moment arm of the respective lever arm to be changed linearly with the force of the spring member.

The present invention also provides a microtome comprising: an object carriage to which a specimen holder mounted; drive means for moving the object carriage up and down in a vertical path; and a mass-balancing arrangement for balancing movable masses of the microtome as mentioned in the above.

A principle of the invention is that the constant force of gravitation produced by the mass of the vertical carriage is counteracted by an equally large force of the lever-spring system. In particular, by virtue of the adjustable load spring and the special design (i.e., the combination of a cam and a sector) of the lever, the two torques, produced at both sides of the lever, can be kept balanced perfectly with each other.

This arrangement makes it possible for the object carriage to be brought to a standstill in every position along its path of movement when no additional accelerating forces are acting on it. For example, when changing a preparation, the object carriage will not inevitably drop to its lower stop position. The object carriage may be held at any position. Consequently, the risk of injury to an operator due to an uncontrolled carriage movement, such as a sudden, vertical drop, decreases.

Further features and advantages of the present invention will become apparent from the following description of exemplary embodiments thereof taken in conjunction with the accompanying drawings, in which like numerals indicate like parts.

DETAILED DESCRIPTION OF THE PREFERRED EMBODIMENTS

Figure 1:
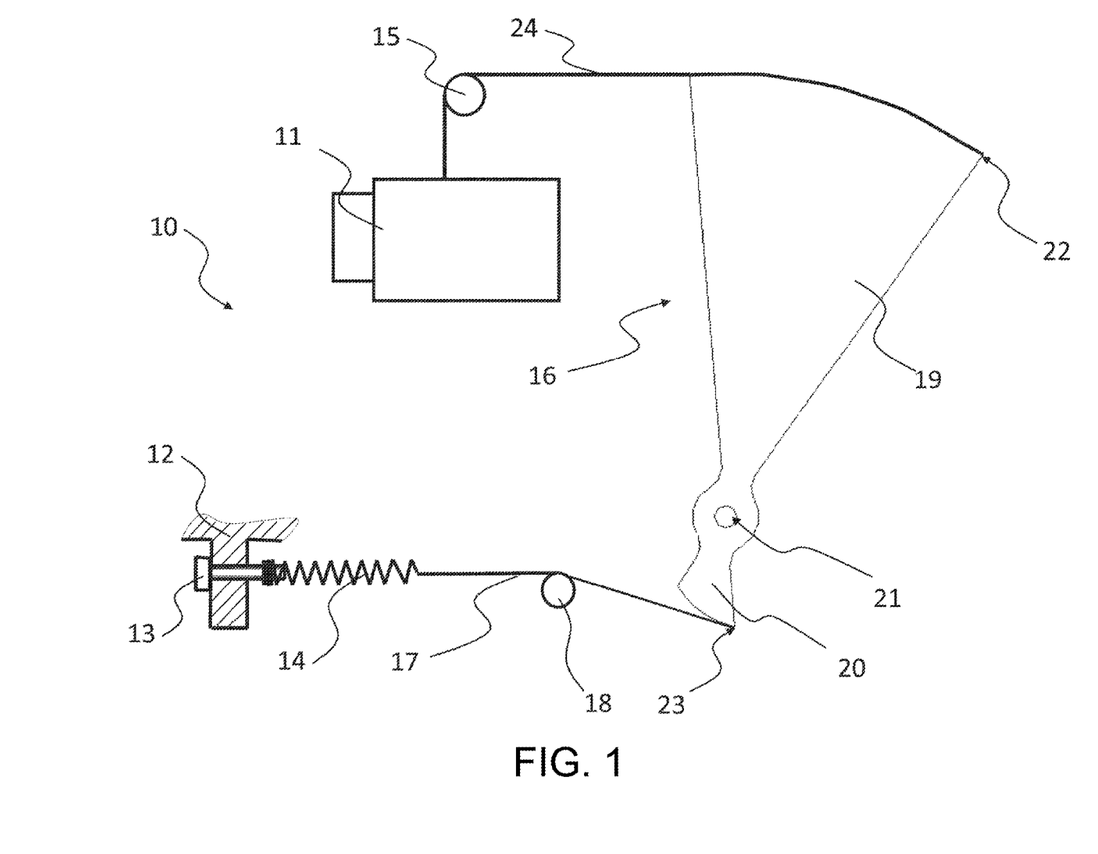
FIG. 1 is a schematic view showing a mass-balancing arrangement of a rotary microtome according to a first embodiment of the present invention, in which an object carriage is at a highest position.
Figure 2:
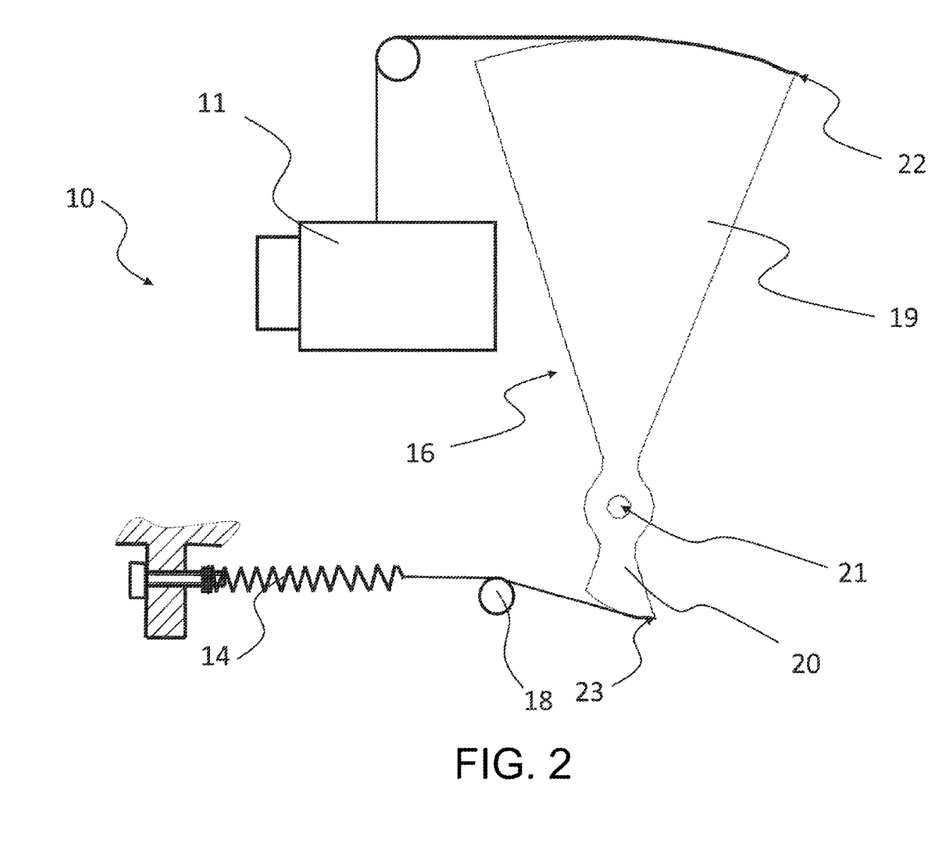
FIG. 2 is a schematic view showing the mass-balancing arrangement according to the first embodiment of the present invention, in which the object carriage is at an intermediate position.
Figure 3:
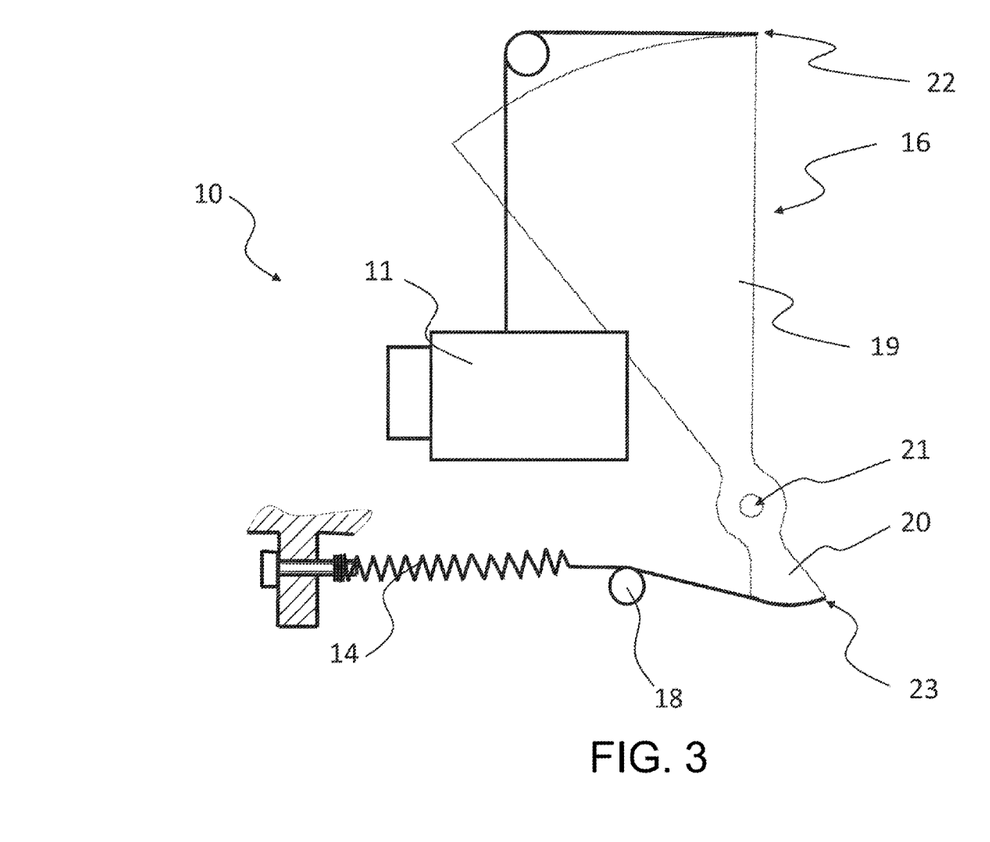
FIG. 3 is also a schematic view showing the mass-balancing arrangement according to the first embodiment of the present invention, in which the object carriage is at a lowest position.

FIGS. 1-3 show a mass-balancing arrangement 10 of a microtome according to a first embodiment of the present application.

Although the figures do not show the details, the skilled person in the art should understand that the microtome generally comprises: an object carriage to which a specimen holder is mounted; drive means for moving the object carriage up and down in a vertical path; and a mass-balancing arrangement for balancing movable masses of the microtome. The "movable masses" include all of the moveable components of the microtome, in particular, they include the object carriage, the specimen holder, the specimen and other movable parts such as a hand wheel, a flywheel. The microtome structure described above is shown and described in aforementioned U.S. Pat. No. 5,881,626, the entire disclosure of which is incorporated herein by reference.

Referring to FIG. 1, the mass-balancing arrangement 10 according to the first embodiment of the present invention comprises: a pre-loaded, adjustable spring member 14; a pivotably mounted lever 16 for compensating different inertial forces in combination with the spring member 14; a first drawing member 24 for connecting an object carriage 11 to the lever 16; a second drawing member 17 for connecting the spring member 14 to the lever 16; and a first roller 15 for deflecting the first drawing member 24. Preferably, it further comprises a second roller 18 for deflecting the second drawing member 17. With the second roller 18, it may shorten the distance between the spring and the lever 16.

The lever 16 is pivotably mounted, for example, by a pivot pin 21, on a holder. The lever 16 has an upper lever arm 19 and a lower lever arm 20. In the first embodiment, the upper lever arm 19 is sector-shaped and has a first outer end surface of a circular-arc shape, while the lower lever arm 20 is cam-shaped and has a second outer end surface of a cam-surface shape. Further, the first drawing member 24, such as a rope, a wire or a chain, is fixedly coupled to a distal end 22 (the right end in FIG. 1) of the first outer end surface of the upper lever arm 19 so that in FIG. 1 the first drawing member 24 is contact with the whole first outer end surface.

The spring member 14, for example, a tensioning spring, has a first end connecting to a base frame 12 of the microtome and a second end connecting to the lower lever arm 20 through the second drawing member 17 (for example, a rope, a wire or a chain). Preferably, the first end of the spring member 14 can be connected through an adjustable tensioning screw 13 so that the spring member 14 can be pre-loaded in tension as desired. It is feasible that the second drawing member 17 is integrally formed with the second end of the spring member 14. Further, the second drawing member 17 (or the second end of the spring member 14) is fixedly coupled to a distal end 23 (the right end in FIG. 1) of the second outer end surface of the lower lever arm 20.

It should be understood that, in addition to being connected to the distal end of the outer end surfaces of the upper and lower lever arms, the first drawing member 24 and the second drawing member 17 can also be connected to other specially designed positions so long as the two torques, produced at both sides of the lever 16, are equal to each other.

Referring to FIG. 2, when the object carriage 11 is moved downwardly, the lever 19 is rotated or pivoted counter clockwise about the pivot pin 21 so that the spring member 14 is pulled to be extended. It should be appreciated that at the side of the upper lever arm 19, the moment arm remains constant due to the circular-arc shape of the first outer end surface of the upper lever arm 19, while the acting force (i.e., the weight of the object carriage 11 and the like) also remains constant. However, at the side of the lower lever arm 20, the moment arm is decreased due to the cam-surface shape of the second outer end surface of the lower lever arm 20, while the acting force (i.e., the spring force of the spring member 14) is increased by the extension of the spring member 14. The contour of the cam of the lower lever arm is designed so that it enables the moment arm of the lower lever arm 20 to be changed linearly with the spring force.

Thus, in the intermediate position of the object carriage as shown in FIG. 2, the product of the moment arm and the acting force at the side of the upper lever arm 19 remains constant, while the product of the moment arm and the spring force at the side of the lower lever arm 20 also remains constant. That is, two torques, produced at both sides of the lever 16, are kept balanced with each other. In this situation, a perfect balance can be reached.

Referring to FIG. 3, when the object carriage 11 moves to the lowest position, for the same reasons as set forth in the above, two torques, produced at both sides of the lever 16, are also kept balanced with each other so that a perfect balance can be reached.

Figure 4:
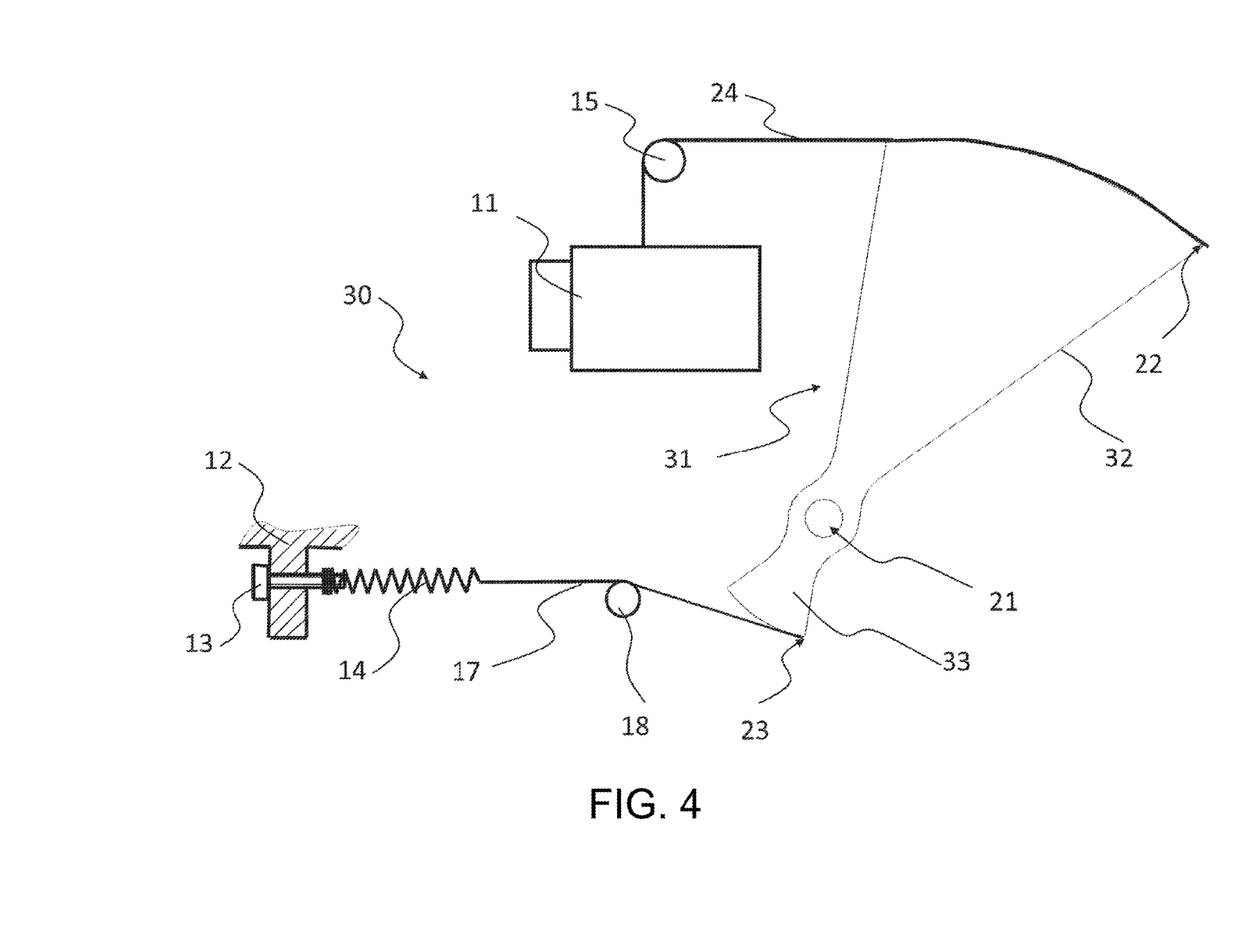
FIG. 4 is a schematic view showing a mass-balancing arrangement of the rotary microtome according to a second embodiment of the present invention, in which the object carriage is at the highest position.
Figure 5:
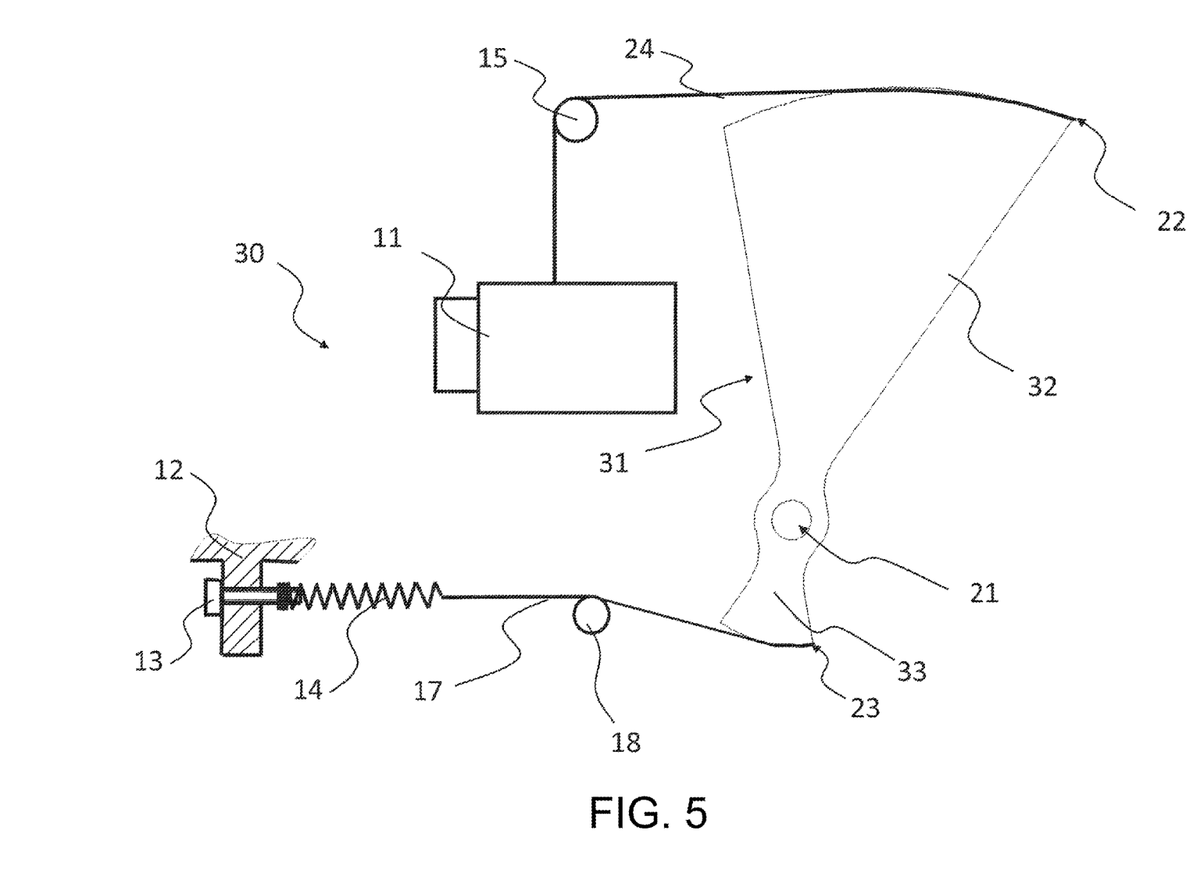
FIG. 5 is a schematic view showing the mass-balancing arrangement according to the second embodiment of the present invention, in which the object carriage is at the intermediate position.
Figure 6:
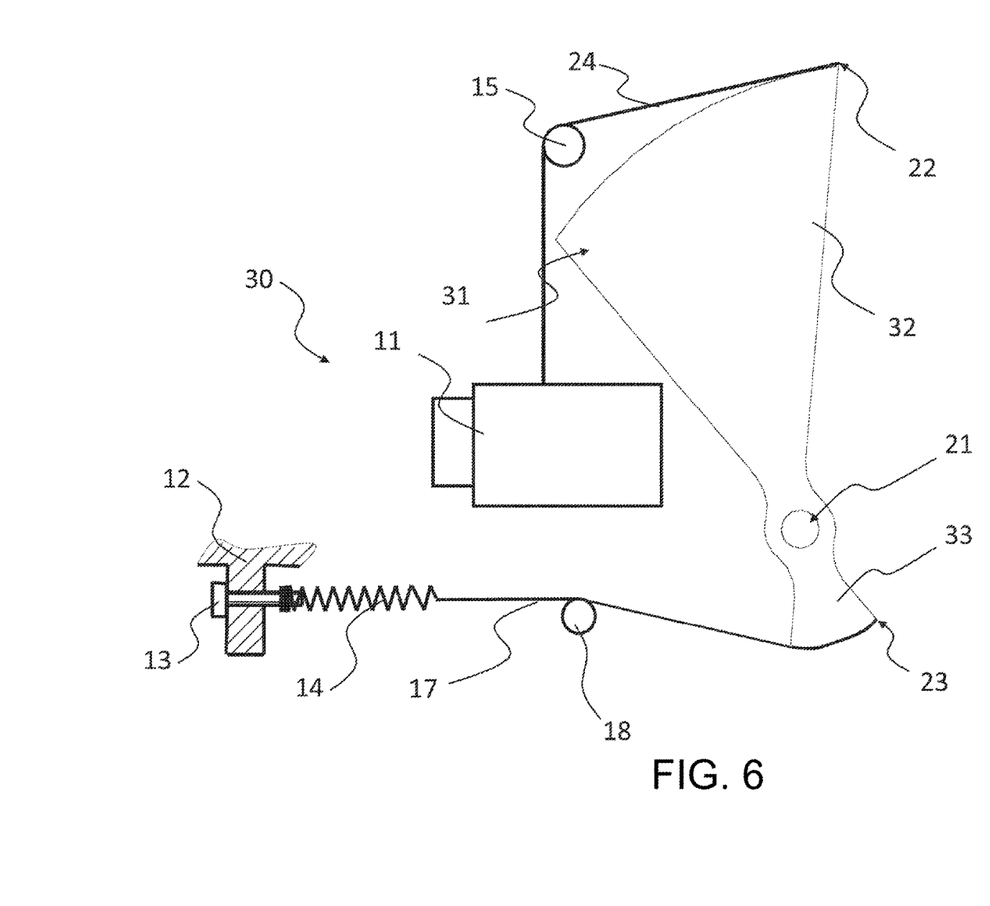
FIG. 6 is also a schematic view showing the mass-balancing arrangement according to the second embodiment of the present invention, in which the object carriage is at the lowest position.

FIGS. 4-6 show a mass-balancing arrangement 30 according to the second embodiment of the present application.

The second embodiment is similar to the first embodiment as shown in FIGS. 1-3, and merely differs in the design of the lever. For conciseness, only the differences regarding the lever will be described hereinafter.

According to the second embodiment, the lever 31 has an upper lever arm 32 and a lower lever arm 33. However, unlike the first embodiment, the upper lever arm 32 is cam-shaped and has a third outer end surface of a cam-surface shape, while the lower lever arm 33 is sector-shaped and has a fourth outer end surface of a circular-arc shape.

Although the lever 31 of the second embodiment is different from the lever 16 of the first embodiment, just similar to the first embodiment, the first drawing member 24 is fixedly coupled to a distal end 22 (the right end in FIG. 4) of the third outer end surface of the upper lever arm 32 so that in FIG. 4 the first drawing member 24 is contact with the whole third outer end surface. And, the second drawing member 17 (or the second end of the spring member 14) is fixedly coupled to a distal end 23 (the right end in FIG. 1) of the fourth outer end surface of the lower lever arm 33.

Referring to FIG. 5, when the object carriage 11 is moved downwardly, the lever 31 is rotated or pivoted counter clockwise about the pivot pin 21 so that the spring member 14 is pulled to be extended. It should be appreciated that at the side of the upper lever arm 32, the moment arm is increased due to the cam-surface shape of the third outer end surface of the upper lever arm 32, while the acting force (i.e., the weight of the object carriage and the like) also remains constant. However, at the side of the lower lever arm 33, the moment arm remains constant due to the circular-arc shape of the fourth outer end surface of the lower lever arm 33, while the acting force (i.e., the spring force of the spring member 14) is increased by the extension of the spring member 14. The contour of the cam surface of the upper lever arm 32 is so designed that it enables the moment arm of the upper lever arm 32 to be changed linearly with the spring force.

Thus, in the intermediate position of the object carriage as shown in FIG. 5, the product of the moment arm and the acting force at the side of the upper lever arm 32 and the product of the moment arm and the spring force at the side of the lower lever arm 33 can be remained equivalent to each other. That is, the two torques, produced at both sides of the lever 31, are kept balanced with each other. In this situation, a perfect balance can be reached.

Referring to FIG. 6, when the object carriage 11 moves to the lowest position, for the same reasons as set forth in the above, the two torques, produced at both sides of the lever 31, are also kept balanced with each other so that a perfect balance can be reached.

Although the present invention has been described with respect to one or more particular embodiments, it should be understood that other embodiments of the present invention may be made without departing from the spirit and scope of the present invention.

LIST OF REFERENCE NUMERALS 10, 30 mass-balancing arrangement
11 object carriage
12 base frame
13 adjustable tensioning screw
14 spring member
15 first roller
16, 31 lever
17 second drawing member
18 second roller
19, 32 upper lever arm
20, 33 lower lever arm
21 pivot pin
22, 23 distal end
24 first drawing member

What is claimed is:

1. A mass-balancing arrangement comprising:
a pre-loaded spring member (14);
a lever (16, 31) pivotable about a pivot pin (21), the lever having an upper lever arm (19, 32) and a lower lever arm (20, 33) on opposite sides of the pivot pin, wherein one of the upper and lower lever arms includes an outer end surface having a circular-arc contour, and another of the upper and lower lever arms includes an outer end surface having a cam contour;
a first drawing member (24) connecting the upper lever arm (19, 32) to a movable mass, wherein a first torque is developed about the pivot pin; and
a second drawing member (17) connecting the lower lever arm (20, 33) to the spring member (14), wherein a second torque is developed about the pivot pin in an angular direction opposite the first torque; and
a first roller (15) for deflecting the first drawing member (24);
wherein the first torque and the second torque are kept balanced with each other during displacement of the movable mass;
wherein the first drawing member (24) is fixedly coupled to a distal end (22) of the outer end surface of the upper lever arm (19, 32), and the second drawing member (17) is fixedly coupled to a distal end (23) of the outer end surface of the lower lever arm (20, 33); and
wherein a varying portion of the first drawing member (24) is in contact with the outer end surface of the upper lever arm (19, 32) defining a first release point where the first drawing member (24) is no longer in contact with the outer end surface of the upper lever arm (19, 23), and a varying portion of the second drawing member (17) is in contact with the outer end surface of the lower lever arm (20, 33) defining a second release point where the second drawing member (17) is no longer in contact with the outer end surface of the lower lever arm (20, 33), such that the first release point, the pivot pin (21), and the second release point are collinear and remain collinear throughout the displacement of the movable mass.

2. The mass-balancing arrangement according to claim 1, further comprising a second roller (18) for deflecting the second drawing member (17).

3. The mass-balancing arrangement according to claim 1, wherein the upper lever arm (19) includes the outer end surface having the circular-arc contour, and the lower lever arm (20) includes the outer end surface having the cam contour.

4. The mass-balancing arrangement according to claim 3, wherein the upper lever arm (19) is sector-shaped.

5. The mass-balancing arrangement according to claim 1, wherein the upper lever arm (32) includes the outer end surface having a cam contour, and the lower lever arm (33) includes the outer end surface having a circular-arc contour.

6. The mass-balancing arrangement according to claim 5, wherein the lower lever arm (33) is sector-shaped.

7. The mass-balancing arrangement according to claim 5, wherein the first drawing member (24) is fixedly coupled to a distal end (22) of the outer end surface of the upper lever arm (32), while the second drawing member (17) is fixedly coupled to a distal end (23) of the outer end surface of the lower lever arm (33).

8. The mass-balancing arrangement according to claim 1, wherein the pre-loaded spring member (14) is a tension spring member, and a first end of the spring member (14) is connected to a base frame (12) through an adjustable tensioning screw (13).

9. The mass-balancing arrangement according to claim 1, wherein the outer end surface having a cam contour is designed to enable the moment arm of the associated lever arm to change linearly with the force of the spring member as the lever pivots about the pivot pin.

10. A microtome comprising:
an object carriage to which a specimen holder is mounted;
drive means for moving the object carriage up and down in a vertical path; and
a mass-balancing arrangement for balancing the object carriage, the mass-balancing arrangement comprising:
a pre-loaded spring member (14);
a lever (16, 31) pivotable about a pivot pin (21), the lever having an upper lever arm (19, 32) and a lower lever arm (20, 33) on opposite sides of the pivot pin, wherein one of the upper and lower lever arms includes an outer end surface having a circular-arc contour, and another of the upper and lower lever arms includes an outer end surface having a cam contour;
a first drawing member (24) connecting the upper lever arm (19, 32) to the object carriage, wherein a first torque is developed about the pivot pin;
a second drawing member (17) connecting the lower lever arm (20, 33) to the spring member (14), wherein a second torque is developed about the pivot pin in an angular direction opposite the first torque; and
a first roller (15) for deflecting the first drawing member (24);
wherein the first torque and the second torque are kept balanced with each other during displacement of the object carriage;
wherein the first drawing member (24) is fixedly coupled to a distal end (22) of the outer end surface of the upper lever arm (19, 32), and the second drawing member (17) is fixedly coupled to a distal end (23) of the outer end surface of the lower lever arm (20, 33); and
wherein a varying portion of the first drawing member (24) is in contact with the outer end surface of the upper lever arm (19, 32) defining a first release point where the first drawing member (24) is no longer in contact with the outer end surface of the upper lever arm (19, 23), and a varying portion of the second drawing member (17) is in contact with the outer end surface of the lower lever arm (20, 33) defining a second release point where the second drawing member (17) is no longer in contact with the outer end surface of the lower lever arm (20, 33), such that the first release point, the pivot pin (21), and the second release point are collinear and remain collinear throughout the displacement of the movable mass.

11. The mass balancing arrangement according to claim 1, wherein the first drawing member (24) is conformable to the outer end surface of the upper lever arm (19, 32), and the second drawing member (17) is conformable to the outer end surface of the lower lever arm (20, 33).

12. The mass balancing arrangement according to claim 10, wherein the first drawing member (24) is conformable to the outer end surface of the upper lever arm (19, 32), and the second drawing member (17) is conformable to the outer end surface of the lower lever arm (20, 33).

* * * * *